United States Patent [19]

Ledig, deceased et al.

[11] 4,288,595
[45] Sep. 8, 1981

[54] 7-(SUBSTITUTED)-7H-PYRROLO[3,2-f]QUINAZOLINE-1,3-DIAMINES

[75] Inventors: Kurt W. Ledig, deceased, late of Philadelphia, Pa.; by David R. Howes, executor, Baltimore, Md.

[73] Assignee: American Home Products Corporation, New York, N.Y.

[21] Appl. No.: 143,228

[22] Filed: Apr. 24, 1980

[51] Int. Cl.³ ................. C07D 487/04; A61K 31/505
[52] U.S. Cl. ..................................... 544/250; 424/251
[58] Field of Search ........................ 544/250; 424/251

[56] References Cited

U.S. PATENT DOCUMENTS 3,850,957  11/1974  White et al. ................... 544/252 X
4,118,561  10/1978  Ledig ............................... 542/470

*Primary Examiner*—Donald G. Daus
*Assistant Examiner*—Diana G. Rivers
*Attorney, Agent, or Firm*—George Tarnowski

[57] ABSTRACT

7-(Substituted)-pyrrolo[3,2-f]quinazoline-1,3-diamines possess antibacterial activity in vitro. The invention also provides compounds having in vivo activity against malarial infections.

11 Claims, No Drawings

7-(SUBSTITUTED)-7H-PYRROLO[3,2-F]QUINAZOLINE-1,3-DIAMINES

Various derivatives of 2,4-diaminoquinazoline and 2,4,6-triaminoquinazoline are described in the literature and are known to possess antifolic activity in bacterial systems. Such compounds are also known to exhibit antibacterial or antiprotozoal activity. For example, 2,4-diaminoquinazolines having an alkyl group at the 5-position and/or 6-position or having a trimethylene bridge between the 5- and 6-position possess antibacterial activity [See Hitchings et al., U.S. Pat. No. 2,945,859 or De Graw et al., J. Med. Chem., 17, 762 (1974)]. 2,4-Diamino-6-[(arylmethyl)-amino]quinazolines; 2,4-diamino-6-{[(substituted aryl)methyl]-amino}-quinazolines; and 2,4-diamino-6-{[(heterocyclic)methyl]-amino}-quinazolines along with derivatives having a 5-alkyl substituent or $N^6$-alkyl substituent exhibit antimalarial activity. [See Davoll et al., J. Med. Chem., 15, 812 (1972); Elslager et al., J. Med. Chem., 15, 1138 (1972); see also the review article by E. Elslager entitled, "New Perspectives on the Chemotherapy of Malaria, Filariasis, and Leprosy," Progress in Drug Research 18, 99,172 (1974), in particular pages 111-116 and 152-154].

The pyrrolo[3,2-f]quinazoline-1,3-diamines of the invention differ from the known 2,4,6-triaminoquinazolines in that the 5-position and the $N^6$ position of the latter are bridged by an ethylene moiety thus forming a novel tricyclic heterocycle.

The invention sought to be patented comprises compounds of the formula:

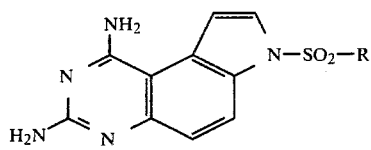

I or a non-toxic acid addition salt thereof,
wherein:
R is phenyl, 4-nitrophenyl, 4-methylphenyl, 4-t-butylphenyl, 4-methoxyphenyl, 4-chlorophenyl, 4-(acetylamino)phenyl, 3-trifluoromethyl)phenyl, 2,4-dimethylphenyl, 3,4-dichlorophenyl, or 2-naphthyl.

The compounds of Formula I, wherein R is as hereinbefore defined or the salts thereof, inhibit the growth of bacteria in vitro as demonstrated in a standard tube dilution test employing seed agar or Wellcotest Sensitivity Test Agar fortified with 5% hemolyzed horse blood as the growth medium. The compounds have shown activity in vitro against one or more of the following strains of bacteria: *S. aureus* Smith, *S. aureus* 53-180, *N. catarrhalis* 8193, *E. coli* 9637, *S. paratyphi* 11737, *K. pneumoniae* 10031, or *P. vulgaris* 6896.

The compounds of the invention also have antimalarial activity in vivo as evidenced by a standard blood schizonticidal test in mice infected with *Plasmodium berghei* KBG173.

In general, the compounds of Formula I having an $N^7$-substituent are prepared by reacting 7-$\underline{H}$-pyrrolo[3,2-f]quinazoline-1,3-diamine with an alkali metal base to form the corresponding alkali metal salt, and the salt is reacted with the appropriate reagent, $RSO_2$-Z, in order to attach the desired substituent, $RSO_2$- at the 7-position. The base employed in the first step must be of sufficient strength to remove the proton from the indolic nitrogen of the starting material. Examples of such bases are sodium and potassium hydride, potassium t-butoxide, and lithium or potassium amide.

In the reagent $RSO_2$-Z, R is as defined hereinbefore with respect to Formula I and Z is a leaving group.

In the reagent $RSO_2$-Z, the preferred leaving group Z is a chlorine, bromine, or iodine atom. Other examples, of appropriate leaving groups (Z) for $RSO_2$-Z are tosyloxy or mesyloxy. The reaction is conveniently carried out in an inert solvent, such as dimethylformamide (DMF) or dimethylactamide (DMA). In a preferred method, the 7-$\underline{H}$-pyrrolo[3,2-f]quinazoline-b 1,3-diamine is treated with sodium-hydride in dimethylformamide and the appropriate reagent $RSO_2$-Z is added to the reactin mixture.

7-$\underline{H}$-Pyrrolo[3,2-f]quinazoline-1,3-diamine is prepared by heating an acid addition salt of 5-aminoindole at a temperature of about 185°-215° C. with an alkali metal dicyanamide, such as sodium or potassium dicyanamide, in an aliphatic alcohol solvent. Best results are achieved if a >2:1 molar ratio of the dicyanamide to the 5-aminoindole acid addition salt is employed. A molar ratio of about 2.5:1 is preferred. The reaction is conveniently carried out by heating the reactants at the reflux temperature of the solvent. Aliphatic alcohols having a boiling point of about 185° C. to about 215° C. are preferred solvents. In a preferred method, the 5-aminoindole acid addition salt is heated at reflux temperature in 1-octyl alcohol with sodium dicyanide until the reaction is complete.

The starting materials which are 5-aminoindole and the reagent $RSO_2$-Z are either known compounds or can be prepared by known methods for analogous compounds or by obvious modifications of the known methods.

The compounds of Formula I may be isolated and purified either in the form of the free bases or the acid addition salts. Methods for converting one such form to another will be obvious to one skilled in the art of chemistry.

For pharmacological use, the compounds of Formula I may be administered in the form of an acid addition salt of a nontoxic organic or inorganic acid. The salts may be prepared by methods well known in the art. Appropriate salts are those formed from the following acids: hydrochloric, hydrobromic, maleic, benzoic, pamoic, methanesulfonic, or acetic.

For pharmacological use, the compounds of Formula I may be administered alone or in combination with pharmaceutically acceptable carriers, the proportion and nature of which are determined by the solubility and chemical properties of the compound selected, the chosen route of administration, and standard pharmaceutical practice. For example, the compounds of Formula I may be administered orally in solid dosage forms, e.g. capsules, tablets, or powders, or in liquid forms, e.g. solutions or suspensions. The compounds may also be injected parenterally in the form of sterile solutions or suspensions. Solid oral forms may contain conventional excipients, for instance, lactose, sucrose, magnesium stearate, resins, and like materials. Liquid oral forms may contain various flavoring, coloring, preserving, stabilizing, solubilizing or suspending agents. Parenteral preparations are sterile aqueous or non-aqueous solutions or suspensions which may contain various preserving, stabilizing, buffering, solubilizing, or suspending agents. If desired, additives, such as saline or glucose may be added to make the solutions isotonic.

The following examples are illustrative of the methods of making and using the compounds of the invention. All temperatures are in centigrade.

EXAMPLE 1

7-H-Pyrrolo[3,2-f]Quinazoline-1,3-Diamine

A suspension of 168.6 g. 5-aminoindole hydrochloride (prepared by treating a methanolic suspension of 5-aminoindole with excess isopropanolic hydrogen chloride and diluting the salt solution with ether), 222 g. sodium dicyanamide (previously recrystallized from methanol), and 3 l. 1-octanol are refluxed with thorough stirring (under nitrogen) for 13 hours, and the hot mixture is filtered. The insolubles are washed with 500 ml. hot 1-octanol; the combined filtrates are diluted with an equal volume of ether and are acidified to pH 1 with isopropanolic hydrogen chloride. A fine, yellow precipitate is collected by filtration (slow) and is dissolved in 3 l. warm water. The aqueous solution is filtered through a coarse, sintered glass funnel. Upon cooling to ca. 25° C., the solution is washed with ethyl acetate and with ether. Basification of the solution with aqueous sodium hydroxide affords a yellow precipitate which is collected, thoroughly washed with water and dried to constant weight. The crude product (141.5 g.) is dissolved in ca. 10 l. methanol, treated with charcoal, and filtered thru Celite. The methanolic solution is concentrated to a volume of ca. 400 ml., diluted with 200 ml. acetone and chilled.

The solid that separates is washed with cold acetone and is dried to provide 77.6 g. of the title compound, m.p. 263°–265° (dec.). An additional 17.2 g. of product [m.p. 262°–264° (dec.)] are isolated by concentrating the crystallization mother liquor to a volume of ca. 40 ml., adding 40 ml. acetone, and chilling. Recrystallization of a 1.0 g. quantity of product [m.p. 263°–265° (dec.)] from methanol-acetone gives 395 mg. title compound, m.p. 264° (dec.); NMR (dDMSO): δ7.14 (doublet, J=3 Hz, 9H), 7.20 (doublet, J=9 Hz, 5 or 6H), 7.54 (doublet, J=3 Hz, 8H), 7.78 (doublet, J=9 Hz, 5 or 6H), 11.65 (broad singlet, exchange-able, 7H) p.p.m.; $\lambda_{max}^{95\% EtOH}$ 232.5 ($\epsilon$24,300), 358 ($\epsilon$22,120), 312 ($\epsilon$8,090), 340.5 ($\epsilon$7.420) nm; $\lambda_{min}^{95\% EtOH}$ 250 ($\epsilon$20,940), 279 ($\epsilon$2,310), 330 ($\epsilon$7,140) nm.

7-H-Pyrrolo[3,2-f]quinazoline-1,3-diamine (5.62 g. prepared in a manner similar to that described above) in 300 ml. methanol is treated with excess isopropanolic hydrogen chloride, and the solution is concentrated to a volume of ca. 100 ml., diluted with 200 ml. dimethoxyethane, and thoroughly cooled. The salt is collected and dried. Weight 2.7 g. Concentration of the mother liquor provides an additional 3.8 g. salt. Recrystallization of the two solids from methanol-ethanol yields 5.26 g. title compound as the monohydrochloride salt, m.p. >310°.

Analysis for: $C_{10}H_9N_5 \cdot HCl$, Calculated: C, 50.96; H, 4.28; N, 29.72; Cl, 15.05, Found: C, 50.81; H, 4.22; N, 30.01; Cl, 14.88.

Employing conditions similar to those above, A. Rosowsky and N. Papathanasopoulos [J. Org. Chem., 39, 3293 (1974)] converted naphthylamines into 2,4-diaminobenzo[h]quinazolines.

EXAMPLE 2

7-[(2,5-Dimethylphenyl)Sulfonyl]-7H-Pyrrolo-[3,2-f]Quinazoline-1,3-Diamine

A solution of 11.97 g. 7H-pyrrolo[3,2-f]quinazoline-1,3-diamine, as prepared in Example 1, in 750 ml. dry dimethylformamide is stirred under nitrogen as 3.18 g. of ca. 50% sodium hydride-mineral oil is added carefully. After stirring for 1.5 hours and chilling with an ice-water bath, a solution of 13.51 g. 2,5-dimethylbenzenesulfonyl chloride in 50 ml. dry dimethylformamide is added dropwise to the chilled stirring suspension. Stirring is continued for 4 hours, while the reaction slowly warms to ambient temperature, and is quenched with 30 ml. isopropanol. After removal of solvent (in vacuo), the residue is stirred thoroughly with excess aqueous potassium carbonate solution and filtered. The solids are collected, washed well with water, rinsed with hexane, and dried. The crude product is dissolved in 2.5 liters of boiling methanol, treated with charcoal, and filtered through Celite. The filtrate is concentrated to ca. 1 liter and chilled. The crystalline solid is collected and again recrystallized from methanol and dried to afford 9.68 g. of the title compound, m.p. 271.5°–272.5° C., NMR (d DMSO): δ2.35 (singlet, 5—CH₃), 2.39 (singlet, 2—CH₃), 5.93 (singlet, 3—NH₂), 6.88 (singlet, 1—NH₂), 7.16 (doublet, J=9 cps, 5H), 7.48 (doublet, J=3½ cps, 9H), 8.9 (doublet, J=3½ cps, 8H) p.p.m.; $\lambda_{max}^{95\% EtOH}$ 242 shoulder ($\epsilon$28,300), 257 ($\epsilon$31,700), 288 shoulder ($\epsilon$12,500), 350 ($\epsilon$4,900) nm; $\lambda_{min}^{95\% EtOH}$ 320 ($\epsilon$2,700) nm.

EXAMPLES 3–12

Employing conditions similar to those recorded in Example 2, 7H-pyrrolo[3,2-f]quinazoline-1,3-diamine is reacted with the appropriately substituted sulfonyl chloride to provide the 7-(substituted)sulfonyl-7H-pyrrolo[3,2-f]quinazoline-1,3-diamines described in Table I.

TABLE I

| Example Number | R | Recryst solvent | m.p., °C. |
|---|---|---|---|
| 3 | 4-nitrophenyl | MeOH | 254–255 (d) |
| 4 | 2-naphthyl | MeOH | 293–294 (d) |
| 5 | 4-methylphenyl | MeOH | 283 (d) |
| 6 | 4-methoxyphenyl | MeOH | 263 |
| 7 | 3,4-dichlorophenyl | DMF | 264 (267) |
| 8 | 4-chlorophenyl | MeOH | 285–287 |
| 9 | 3-trifluoromethyl-phenyl | MeOH | 258.5–259.5 |
| 10 | phenyl | MeOH | 272.5–274.5 |
| 11 | 4-(acetylamino)phenyl | DMF/H₂O | 300–302 |
| 12 | 4-(t-butyl)phenyl | MeOH | 262–263 |

EXAMPLE 13

The ability of the compounds of Formula I to inhibit the growth of bacteria in vitro is demonstrated in the following test procedure:

A stock solution or suspension of the test compound at a concentration of 2500 μg/ml. is prepared utilizing a suitable solvent or medium such as aqueous sodium hydroxide, aqueous lactic acid, methyl cellosolve, dimethylsulfoxide, dimethylacetamide, ethylene glycol, dimethylformamide, formamide, propylene glycol, acetone or methanol. Two-fold dilutions are made by adding appropriate amounts of sterile water to the solution or suspension of the test substance. One ml. quantities of each dilution are incorporated into Wellcotest Sensitivity Test Agar fortified with 5% hemolyzed horse blood (9 ml. vol.) in sterile Petri dishes to give plates containing varying concentrations of the test compound. The hardened surfaces of each plate are incubated with the test organism, and the plates are incubated for 18 hours at 35° C. The in vitro antibacterial activity of the compounds tested is expressed as the "minimal inhibitory concentration" (MIC) which is defined as the least amount of material ($\mu$g/ml.) that completely inhibits the test organism.

The in vitro antibacterial activities of compounds of the invention are set forth in Table II below which sets forth the MIC values of various compounds when tested according to the above-described procedure:

Test compounds are administered after dissolution or suspension in peanut oil. A single dose is given subcutaneously 72 hours after the mice are infected with *Plasmodium berghei*. At this time a 10-15 percent parasitemia has developed; the disease is well established but has not produced sufficient debility to alter the response of the host to toxic effects of the drug on test. Since treatment is withheld for three days to permit the infection to become well established and death occurs in untreated controls within 6-8 days, it is felt that this system presents a candidate compound with the maximum challenge. In order to check factors such as changes in the infectivity of *Plasmodium berghei* or in the susceptibility of the host or to detect technical errors, a group of infected animals treated with pyrimeth-

TABLE II

In vitro Antibacterial Activity of 7-(Substituted Arylsulfonyl)-7H-Pyrrolo[3,2-f]Quinazoline-1,3-Diamines

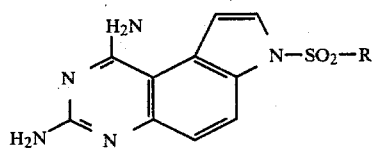

| Compound of Example | R | MIC ($\gamma$/ml.) | | | | | | |
|---|---|---|---|---|---|---|---|---|
| | | S. aureus Smith | S. aureus 53–180 | N. catarrhalis 8193 | E. coli 9637 | S. paratyphi 11737 | K. pneumoniae 10031 | P. vulgaris 6896 |
| 2 | 2,5-dimethylphenyl | 7.81 | 0.976 | — | 31.3 | 31.3 | 31.3 | 62.5 |
| 3 | 4-nitrophenyl | 7.81 | 3.90 | 0.12 | 7.81 | >250 | 3.90 | >250 |
| 4 | 2-naphthyl | 250 | 250 | 15.6 | >250 | >250 | >250 | >250 |
| 5 | 4-methylphenyl | 125 | 62.5 | 1.95 | >250 | >250 | 15.6 | >250 |
| 6 | 4-methoxyphenyl | 15.6 | 7.81 | 0.122 | >250 | >250 | 3.90 | >250 |
| 7 | 3,4-dichlorophenyl | 31.3 | 3.90 | 0.122 | >250 | >250 | 3.13 | >250 |
| 8 | 4-chlorophenyl | 62.5 | 15.6 | 0.244 | >250 | >250 | 7.81 | >250 |
| 9 | 3-(trifluoromethyl)-phenyl | 3.90 | 0.976 | — | >250 | >250 | 3.90 | >250 |
| 10 | phenyl | 1.95 | 0.976 | — | 3.90 | 15.6 | 0.488 | 125 |
| 11 | 4-(acetylamino)phenyl | 31.3 | 31.3 | — | >250 | >250 | 7.81 | >250 |
| 12 | 4-t-butylphenyl | 7.81 | 3.90 | — | 250 | >250 | 1.95 | >250 |

EXAMPLE 14

The antimalarial effects of the compounds of Formula I are demonstrated, and elicited by means of the test procedure described below:

Utilizing young ICR/HA Swiss mice and a standard inoculum of *Plasmodium berghei* KBG 173, it is possible to produce a uniform disease fatal to 100% of untreated animals within 6 to 8 days with a mean survival time of 6.2 days. Test animals weigh from 18 to 22 grams but weight variations in any given experimental or control group are confined to 2-3 grams. All animals in any given test are approximately of the same age. Animals on test are housed in metal-topped plastic cages, given a standard laboratory diet and water ad libitum.

Test animals receive an intraperitoneal injection of 0.5 ml. of 1:100 dilution of heparinized heart's blood with a minimum of 90% parasitized cells (4 $\times$ 10$^7$ cells), drawn from donor mice infected one week earlier with *Plasmodium berghei*. The donor strain is maintained by weekly passages in separate groups of mice inoculated with a 0.5 ml. of 1:500 dilution of heparinized heart's blood.

amine at dose levels producing definite increases in survival time is included in a positive control in every experiment.

In each experiment test compounds are administered in graded dosages. With highly active compounds, increases in dose levels are usually followed by increases in the survival time of the treated mice. However, if an active drug is toxic for the host, its toxicity may become a limiting factor; continued increases in dose levels also increase the toxic effects and may result in the diminution of survival times. Deaths prior to the sixth day, when untreated controls begin to die, are regarded as nonparasitic and become the basis for toxicity evaluations. Treated animals are kept under observation for 60 days. Survivors at the end of this period of time are considered as cured. In calculating mean survival time, toxic deaths and 60-day survivors are not included.

Compounds are considered active which produce a cure in at least one test animal or which produce significant increases in mean survival times of the treated animals as compared with the mean survival times of untreated controls, provided that no drug related deaths (toxicity) are noted at the active dose.

The results of antimalarial testing of compounds of this invention are set forth in Table III.

TABLE III

Activity of 7-(Substituted Arysulfonyl)-7H-Pyrrolo[3,2-f]Quinazoline-1,3-Diamines Against
*Plasmodium berghei* KBG 173 Malaria in Mice (All Doses are mg. per kg., s.c. Administration)

| Compound of Example | R | Highest[a] Non-Lethal Dose | Lowest Dose Curing All Mice | Min. Curing Dose (Cure/Treat) | ΔMST[b] | Dose |
|---|---|---|---|---|---|---|
| 2 | 2,5-dimethylphenyl | 160 | 40 | 20 (3/5) | 6.6 | 5 |
| 3 | 4-nitrophenyl | — | — | 640 (1/5) | 8.4 | 160 |
| 4 | 2-naphthyl | — | — | 20 (4/5) | 11.4 | 10 |
| 5 | 4-methylphenyl | 640 | 80 | 20 (4/5) | 5.8 | 10 |
| 6 | 4-methoxyphenyl | 640 | 160 | 40 (2/5) | — | — |
| 7 | 3,4-dichlorophenyl | 640[c] | 10[c] | 1.25[c] (1/5) | — | — |
| 8 | 4-chlorophenyl | 160[c] | 40[c] | 40[c] (5/5) | — | — |
| 9 | 3-(trifluoromethyl)phenyl | 160 | 40 | 10 (1/5) | 6.6 | 5 |
| 10 | phenyl | — | — | 40 (1/5) | 7.2 | 20 |
| 11 | 4-(acetylamino)phenyl | 320 | 20 | 10 (3/5) | 9.3 | 5 |
| 12 | 4-t-butylphenyl | 640 | 40 | 20 (1/5) | 6.5 | 10 |

[a]This is the highest dose with no deaths for any reason.
[b]This abbreviation indicates the increase in mean survival time of treated animals to untreated controls at the dose indicated in the adjacent column.
[c]Mice alive on day 14 considered "cured".

What is claimed is:

1. A compound of the general formula:

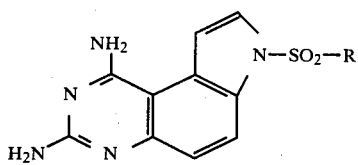

or a non-toxic acid addition salt thereof,
wherein:
R is phenyl, 4-nitrophenyl, 4-methylphenyl, 4-t-butylphenyl, 4-methoxyphenyl, 4-chlorophenyl, 4-(acetylamino)phenyl, 3-(trifluoromethyl)phenyl, 3,4-dichlorophenyl, or 2-naphthyl.

2. The compound as defined in claim 1 wherein R is phenyl.

3. The compound as defined in claim 1 wherein R is 4-nitrophenyl.

4. The compound as defined in claim 1 wherein R is 4-methylphenyl.

5. The compound as defined in claim 1 wherein R is 4-t-butylphenyl.

6. The compound as defined in claim 1 wherein R is 4-methoxyphenyl.

7. The compound as defined in claim 1 wherein R is 4-chlorophenyl.

8. The compound as defined in claim 1 wherein R is 4-(acetylamino)phenyl.

9. The compound as defined in claim 1 wherein R is 3-(trifluoromethyl)phenyl.

10. The compound as defined in claim 1 wherein R is 3,4-dichlorophenyl.

11. The compound as defined in claim 1 wherein R is 2-naphthyl.